United States Patent
Kikuchi et al.

(10) Patent No.: US 11,317,851 B2
(45) Date of Patent: May 3, 2022

(54) SKIN SPOT EVALUATION APPARATUS, SKIN SPOT EVALUATION METHOD AND PROGRAM

(71) Applicant: SHISEIDO COMPANY, LTD., Tokyo (JP)

(72) Inventors: Kumiko Kikuchi, Kanagawa (JP); Yuji Masuda, Kanagawa (JP); Tetsuji Hirao, Kanagawa (JP)

(73) Assignee: SHISEIDO COMPANY, LTD., Tokyo (JP)

(*) Notice: Subject to any disclaimer, the term of this patent is extended or adjusted under 35 U.S.C. 154(b) by 224 days.

(21) Appl. No.: 15/522,880

(22) PCT Filed: Nov. 11, 2015

(86) PCT No.: PCT/JP2015/081769
§ 371 (c)(1),
(2) Date: Apr. 28, 2017

(87) PCT Pub. No.: WO2016/080266
PCT Pub. Date: May 26, 2016

(65) Prior Publication Data
US 2017/0311871 A1    Nov. 2, 2017

(30) Foreign Application Priority Data
Nov. 19, 2014    (JP) .............................. JP2014-234938

(51) Int. Cl.
*A61B 5/00*    (2006.01)
*A61B 5/107*    (2006.01)

(52) U.S. Cl.
CPC ................ *A61B 5/444* (2013.01); *A61B 5/00* (2013.01); *A61B 5/0077* (2013.01); *A61B 5/107* (2013.01); *A61B 5/443* (2013.01); *A61B 5/743* (2013.01)

(58) Field of Classification Search
CPC ......... A61B 5/444; A61B 5/743; A61B 5/443; A61B 5/0077; A61B 5/107; A61B 5/00; A61B 5/441
See application file for complete search history.

(56) References Cited

U.S. PATENT DOCUMENTS 4,693,255 A    9/1987 Beall
2004/0218810 A1*  11/2004  Momma ............... A61B 5/0064
382/162

(Continued)

FOREIGN PATENT DOCUMENTS

CN    101843475    9/2010
EP    1875863    1/2008

(Continued)

OTHER PUBLICATIONS

N. Ojima et al., Image Analysis of Skin Color Using Independent Component Analysis and Its Application to Melanin Pigmentation Analysis, Oleoscience, (Jul. 1, 2007), vol. 7, No. 7, pp. 273 to 277.

(Continued)

*Primary Examiner* — Serkan Akar
*Assistant Examiner* — Aminah Asghar
(74) *Attorney, Agent, or Firm* — IPUSA, PLLC

(57) ABSTRACT

To appropriately evaluate skin spots by grasping a quality (characteristic) of the skin spots. A skin spot evaluation apparatus includes an area extracting unit that extracts skin spot areas corresponding to skin spots from a skin image obtained by photographing a skin of a subject; and an evaluation unit that analyzes, based on the skin spot areas extracted by the area extracting unit, at least one of the number of the skin spots, dimension of each of the skin spots and density of each of the skin spots, and generates data obtained by quantifying characteristic of the skin spots of the skin image using the analyzed result.

6 Claims, 15 Drawing Sheets

(56) References Cited

U.S. PATENT DOCUMENTS

| | | | |
|---|---|---|---|
| 2009/0054744 A1* | 2/2009 | Kitamura | A61B 5/0082 600/306 |
| 2010/0249731 A1 | 9/2010 | Stamatas | |
| 2012/0130697 A1* | 5/2012 | Woodford | A61B 5/0205 703/11 |
| 2013/0202182 A1* | 8/2013 | Rowe | A61B 10/02 382/133 |
| 2014/0100442 A1* | 4/2014 | Begin | A61B 8/466 600/411 |
| 2015/0327805 A1* | 11/2015 | Ben-Haim | A61B 6/5247 600/411 |
| 2016/0171293 A1* | 6/2016 | Li | G06T 7/90 382/103 |
| 2016/0232666 A1* | 8/2016 | Sullivan | G06T 7/155 |
| 2016/0247286 A1* | 8/2016 | Mazurenko | G06K 9/00335 |

FOREIGN PATENT DOCUMENTS

| | | |
|---|---|---|
| JP | H11-299743 | 11/1999 |
| JP | 2000-350702 | 12/2000 |
| JP | 2003-144393 | 5/2003 |
| JP | 2007-020956 | 2/2007 |
| JP | 2007-061307 | 3/2007 |
| JP | 2007-130329 | 5/2007 |
| JP | 2008-245666 | 10/2008 |
| JP | 2010-119431 | 6/2010 |
| JP | 3170125 U | 9/2011 |
| JP | 2013-090751 | 5/2013 |
| WO | 97/47235 | 12/1997 |

OTHER PUBLICATIONS

Y. Masuda et al., Quantification of Face Brown Spots and Freckles with Image Analysis Method, Journal of SCCJ, J. Soc. Cosmet. Chem. Japan, (Sep. 1994) vol. 28, No. 2, pp. 147 to 152.
International Search Report for PCT/JP2015/081769 dated Feb. 9, 2016.
Japanese Office Action for 2014-234938 dated Feb. 2, 2016.
Japanese Office Action for 2014-234938 dated Aug. 30, 2016.
Japanese Office Action for 2014-234938 dated Dec. 20, 2016.
Extended European Search Report for 15860777.0 dated Aug. 2, 2018.
Office Action for 15860777.0 dated Jan. 23, 2020.
Office Action issued in the counterpart Chinese Patent Application No. 201580060618.X, dated Dec. 1, 2020.

* cited by examiner

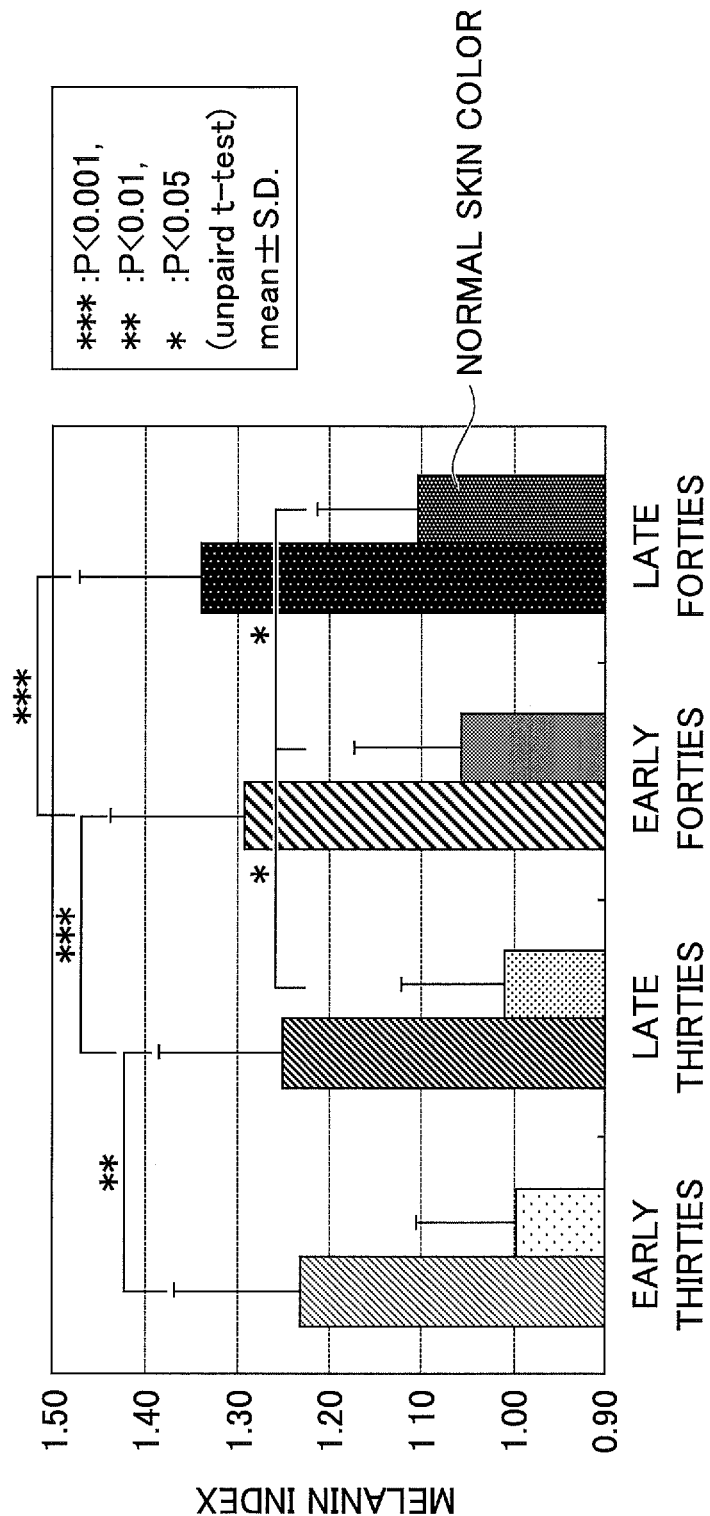

SKIN SPOT EVALUATION APPARATUS, SKIN SPOT EVALUATION METHOD AND PROGRAM

BACKGROUND OF THE INVENTION

1. Field of the Invention

The present invention relates to a skin spot evaluation apparatus, a skin spot evaluation method and a program.

2. Description of the Related Art

A method is known for skin spots or freckles on the entirety of the face, or at an area such as around the eye or the cheek, specified by viewing or the like, for example, by which color data or pigment component data of a skin are quantified using a device such as a spectrophotometer, and the skin spots or the freckles are evaluated based on the quantified color data or the pigment component data of the skin. Quantification of the color data is based on, for example, an average value of principal component scores regarding melanin in a measuring area that are obtained by performing a principal component analysis using spectral reflectance data of a plurality of wavelengths, for example. (see Patent Document 1, for example).

Patent Document

[Patent Document 1] Japanese Laid-open Patent Publication No. 2003-144393

However, the above described method is for determining a degree of distinguishability of targeting skin spots or freckles in a skin area, and a quality (characteristic) of skin spots cannot be quantified by the number of the skin spots, size of each of the skin spots, density of each of the skin spots or the like in a predetermined skin area. Thus, the skin spots cannot be appropriately evaluated because at which timing and how the number of skin spots, their size, density of the skin spots or the like changes is not grasped.

SUMMARY OF THE INVENTION

According to an aspect, the present invention is made to appropriately evaluate skin spots by grasping a quality (characteristic) of the skin spots.

According to an example, there is provided a skin spot evaluation apparatus including an area extracting unit that extracts skin spot areas corresponding to skin spots from a skin image obtained by photographing a skin of a subject; and an evaluation unit that analyzes, based on the skin spot areas extracted by the area extracting unit, at least one of the number of the skin spots, dimension of each of the skin spots and density of each of the skin spots, and generates data obtained by quantifying characteristic of the skin spots of the skin image using the analyzed result.

According to at least one example, it is possible to appropriately evaluate skin spots by grasping a quality (characteristic) of the skin spots.

BRIEF DESCRIPTION OF THE DRAWINGS

FIG. 9 is a view illustrating results obtained by analyzing the density of each of the skin spots based on melanin amounts.

DETAILED DESCRIPTION OF THE PREFERRED EMBODIMENTS

Hereinafter, an embodiment of the invention is described in detail.

(Skin Spot Evaluation Apparatus: Example of Functional Structure)

Figure 1:
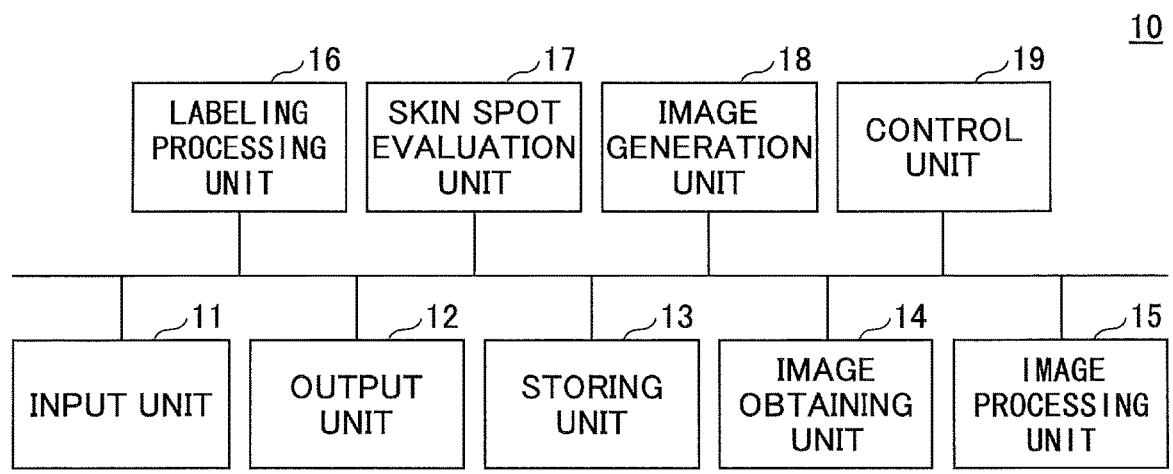
FIG. 1 is a view illustrating an example of a functional structure of a skin spot evaluation apparatus of an embodiment.

FIG. 1 illustrates an example of a functional structure of a skin spot evaluation apparatus of an embodiment. As illustrated in FIG. 1, the skin spot evaluation apparatus 10 includes an input unit 11, an output unit 12, a storing unit 13, an image obtaining unit 14, an image processing unit 15, a labeling processing unit 16, a skin spot evaluation unit 17, an image generation unit 18 and a control unit 19, for example.

The input unit 11 accepts an input of various instructions such as starting/ending or setting regarding a skin spot evaluation process from a user or the like that uses the skin spot evaluation apparatus 10, for example. The input unit 11 is a pointing device such as a keyboard or a mouse, for a general purpose computer such as a PC (Personal Computer), for example. The input unit 11 may be an audio input device such as a microphone capable of inputting the above described input by voice or the like, for example.

The output unit 12 outputs the content input by the input unit 11, a result obtained by a process executed based on the input content or the like. The output unit 12 is a display, a speaker or the like, for example. The output unit 12 may include a printing device such as a printer.

Here, when the skin spot evaluation apparatus 10 is a smartphone, a tablet terminal or the like, for example, the above described input unit 11 and the output unit 12 may have a structure in which input and output are integrally configured such as a touch panel, for example.

The storing unit 13 stores various data necessary in this embodiment. Specifically, the storing unit 13 stores various programs, various setting data or the like for executing the skin spot evaluation process of the embodiment. The storing unit 13 stores a skin image in which the entirety of a cheek of a subject is photographed, analyzed results such as the number of skin spots, dimension of each of the skin spots, density of each of the skin spots in an analyzing area, evaluation results of a quality of the skin spots or the like, for example.

Here, the storing unit 13 stores the above described various data, and may function as a database that is configured to be searched by a keyword or the like, for example. Further, data stored in the storing unit 13 may be obtained from external devices via a communication network, typically Internet, LAN (Local Area Network) or the like.

The image obtaining unit 14 obtains a skin image of a specified portion (around the eye, the cheek or the like, for example) from a face image of a subject photographed by a SIA (Skin Image Analyzer) system or the like that is configured by a diffused illumination box and a digital camera, for example. The image obtaining unit 14 may use, as the SIA system, an apparatus or the like disclosed in registered Japanese Utility Model No. 3170125 of the applicant.

For a lens of the SIA system, EF35 mm F2 (manufactured by Canon Inc.) or the like is used, for example. Alternatively, another commercially available lens whose focal length is different may be used. For a light source of the diffused illumination box of the SIA system, FPL30EX-D (manufactured by Toshiba Corporation) or the like, which is a light source for evaluating color rendering is used, for example.

In a photographing mode of a digital camera of the SIA system, color balance (white balance) is adjusted by manual exposure using a grey color chart, for example. An image size photographed by the SIA system is 4752×3168 pixels or the like, for example. Further, an image photographed by the SIA system is stored in a linear TIFF format (Tagged Image File Format), for example.

However, the structure of the SIA system of the embodiment is not limited to the above described structure.

In the SIA system, it is possible to photograph an image in which reflection at a skin surface, affection of shadow or the like is suppressed by irradiating diffused light, for example, and it is possible to obtain color data of a skin by measuring "color" of a skin in the photographed image.

The image processing unit 15 performs image processing on the skin image obtained by the image obtaining unit 14 and extracts skin spot areas from the analyzing area of the skin image. For example, the image processing unit 15 calculates color data Lab values or a pigment component such as a melanin component or a hemoglobin component in the designated analyzing area in the skin image.

Further, the image processing unit 15 converts the analyzing area to an image that indicates distribution of the pigment component such as the melanin component or the hemoglobin component. The image processing unit 15 converts an image of the analyzing area to an image that indicates distribution of the pigment component such as the melanin component or the hemoglobin component by obtaining RGB values of an RGB color system image photographed by the SIA system, XYZ values of an XYZ color system image converted from the RGB color system image, or the like, as the color data of a skin, for example.

The image processing unit 15 obtains component amounts in the skin by performing a multiple regression analysis using an absorbency model in which transmittance in Lambert-Beer's law is substituted by reflectance of a skin from a reflection spectrum of a skin and an absorption coefficient spectrum of constituting components of the skin, for example. This method is disclosed in Japanese Patent No. 3798550 or the like in detail, for example.

Further, the image processing unit 15 previously obtains a multiple regression equation by a multiple regression analysis using measured color values of the skin and component amounts in the skin, and obtains amounts of a melanin component, a hemoglobin component or the like in the skin from the measured color values of the skin using the multiple regression equation, for example. With this, a melanin component amount is obtained for each pixel of the skin image, for example. This method is disclosed in Japanese Patent No. 3727807 or the like in detail, for example.

Here, RGB values of the image photographed by the SIA system may be converted to CIE-XYZ values, which is an International Standard value, using the following equation, for example.

$$X=0.001645 \times R+0.001116 \times G+0.000314 \times B+2.585143$$

$$Y=0.001110 \times R+0.002080 \times G+0.000065 \times B+2.359088$$

$$Z=0.000439 \times R+0.000610 \times G+0.002439 \times B+2.757769 \quad (1)$$

Further, XYZ values obtained from the above equation (1) may be converted to the pigment component such as the melanin component or the hemoglobin component using the following equation (2) in a method disclosed in the above described Japanese Patent No. 3727807 or the like.

$$\text{Melanin amount}=-4.861 \times \log 10(1/X)+1.268 \times \log 10(1/Y)+4.669 \times \log 10(1/Z)+0.063$$

$$\text{Hemoglobin amount}=-32.218 \times \log 10(1/X)+37.499 \times \log 10(1/Y)-4.495 \times \log 10(1/Z)+0.444 \quad (2)$$

The image processing unit 15 generates an image that indicates density of the pigment component such as the melanin component or the hemoglobin component obtained by the above method and its distribution.

Here, the "skin spot" is generated when pigments are deposited in a skin, and means an area in which the pigments are deposited to a level that an interface between a portion where the pigments are deposited and a portion where the pigments are not deposited is clear in the skin. As main pigment components of the skin spot, the above described melanin component or the hemoglobin component may be raised. In this embodiment, an image (distribution image of the melanin component) that indicates density of the melanin component and its distribution is used, for example, and the quality of the skin spots or its change is analyzed based on the melanin component among the above described pigment components.

Further, the image processing unit 15 removes a low frequency component (a large crinkle corresponding to a shadow, for example) from the distribution image of the melanin component using a bandpass filter (Gaussian function, for example). The image processing unit 15 removes affection of shadow by removing bandwidth whose half width is greater than or equal to about 40.0 mm, for example. With this, affection of shadow due to a shape of a face is removed, for example.

Further, the image processing unit 15 performs a binarization process on the above described analyzing area based on density of the melanin component. In the binarization process, a value that expresses density of the melanin component (melanin value) is used, and a pixel whose melanin value is greater than or equal to a threshold value (high melanin value), while the threshold value is set as an average value+0.01 to 0.30 or the like, is treated as a high melanin portion, for example. With this, normal portions and high melanin portions in the skin are differentiated.

Further, the image processing unit 15 removes noise of the image using a median filter on the above described analyzing area. In the median filter, the noise is removed by using a filter of 5×5 pixels, for example, but not limited so.

The labeling processing unit 16 labels an area where pixels with high melanin values continuously exist as a single pigmentation area (skin spot) in the analyzing area from which the noise of the image is removed by the image processing unit 15. The labeling processing unit 16, when pixels that are identified as the pixels with high melanin values are adjacent to each other, combine these pixels, and extracts a group of combined pixels as a single skin spot area, for example. Further, the labeling processing unit 16 removes areas whose dimension is less than or equal to predetermined dimension (1.0 mm$^2$, for example) from the areas extracted as the skin spots. With this, pores are prevented from wrongly extracted as the skin spots, for example.

The skin spot evaluation unit 17 analyzes the number of the skin spots labeled by the labeling processing unit 16, dimension of each of the skin spots, and density of each of the skin spots, and generates data that is obtained by quantifying a quality (characteristic) of the skin spots obtained from the analyzing area of the skin image using the analyzed results. The skin spot evaluation unit 17 may generate data indicating how the quality of the skin spots changes in accordance with age (generation) of subjects using at least one of the number of the skin spots, dimension of each of the skin spots, and density of each of the skin spots analyzed in skin images of subjects of different ages (generations), for example.

The image generation unit 18 generates a screen in which the skin spots extracted by the image processing unit 15 are displayed. Further, the image generation unit 18 displays the skin spots labeled by the labeling processing unit 16 by different colors in the generated image based on dimension or a diameter of each of the skin spots. Here, a shape of each of the areas labeled as the skin spots may be discriminated, and the dimension or the diameter of each of the skin spots may be calculated based on the discriminated shape, for example. Further, in this embodiment, dimensions of the skin spots may be categorized into a plurality of dimension ranges, and the skin spots categorized into the different dimension ranges may be displayed by different colors, or displayed by different patterns or the like, respectively, for example. Alternatively, the skin spots that are categorized into a certain dimension range may be caused to flash, or the like.

Further, the image generation unit 18 may generate a distribution graph of the labeled skin spots for each dimension or each diameter, or a graph illustrating a change of the quality of the skin spots for each generation by using at least one of the number of the labeled skin spots, the dimension of each of the skin spots and the density of each of the skin spots for each generation.

The control unit 19 controls the entirety of the skin spot evaluation apparatus 10. Further, the control unit 19 controls at least one process among an image processing on a skin image, a labeling process, a skin spot evaluation process or the like, for example.

(Skin Spot Evaluation Apparatus 10: Hardware Structure)

A skin spot evaluation program is generated for having a computer execute each of the functions of the above described skin spot evaluation apparatus 10, and is installed in a general purpose PC, a server or the like, for example. With this, it is possible to actualize the skin spot evaluation process or the like of the embodiment.

Figure 2:
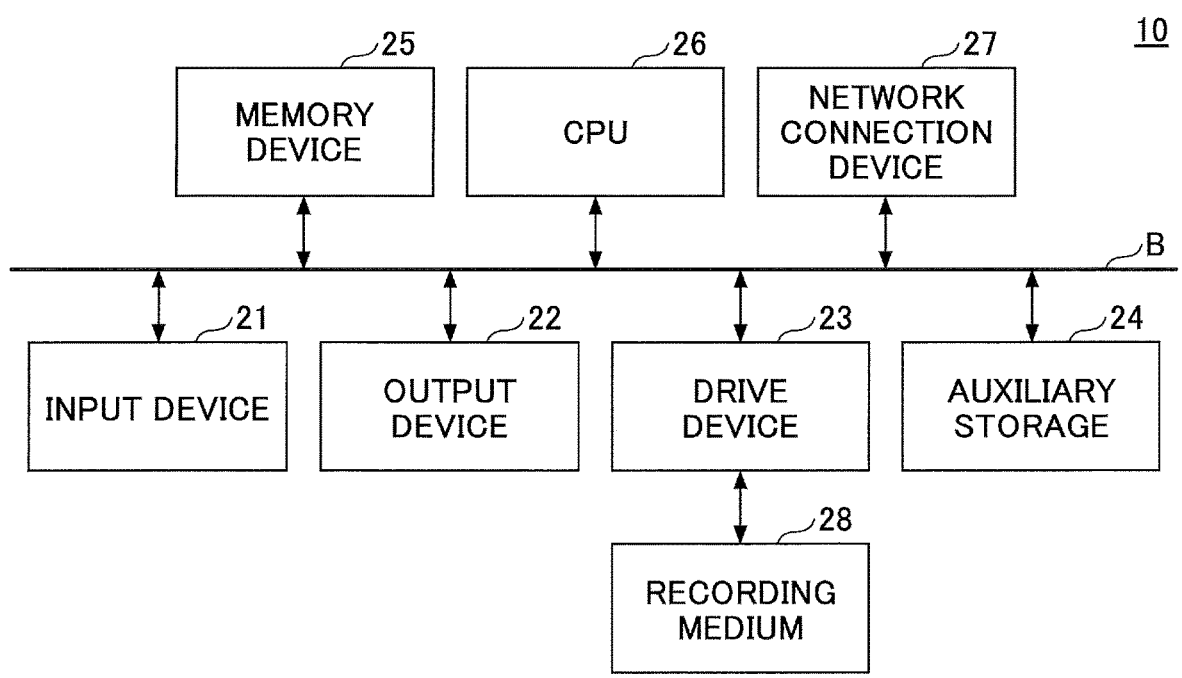
FIG. 2 is a view illustrating an example of a hardware structure capable of performing a skin spot evaluation process.

FIG. 2 is a view illustrating an example of a hardware structure capable of executing the skin spot evaluation process. The computer main body illustrated in FIG. 2 includes an input device 21, an output device 22, a drive device 23, an auxiliary storage 24, a memory device 25, a CPU (Central Processing Unit) 26 that performs various controls and a network connection device 27, and these are connected with each other by a system bus B.

The input device 21 includes a pointing device such as a keyboard or a mouse, and an audio input device such as a microphone that is operated by a user or the like, and inputs various operation signals such as an instruction to execute a program from the user or the like. Further, the input device 21 includes an input unit that inputs a skin image of a subject that is photographed using a diffused illumination box, a digital camera and the like, for example.

The output device 22 includes a display that displays various windows, data or the like necessary for operating the computer main body that performs the processes of the embodiment, and displays progresses, results or the like of processes by a control program executed by the CPU 26.

Here, the skin spot evaluation program that is installed in the computer main body of the embodiment may be provided by a portable recording medium 28 or the like such as a USB (Universal serial Bus) memory or a CD-ROM, for example. The recording medium 28 is capable of being set in the drive device 23. The skin spot evaluation program included in the recording medium 28 is installed in the auxiliary storage 24 from the recording medium 28 via the drive device 23.

The auxiliary storage 24 is a storage unit such as a hard disk, and stores the skin spot evaluation program of the embodiment, the control program or the like, and is capable of inputting and outputting data in accordance with necessity.

The memory device 25 stores the skin spot evaluation program or the like that is read out by the CPU 26 from the auxiliary storage 24. Here, the memory device 25 is a ROM (Read Only Memory), a RAM (Random Access Memory) or the like. Here, the above described auxiliary storage 24 and the memory device 25 may be integrally structured as a single storing device.

The CPU 26 performs various calculations by executing the control program such as an OS (Operating system), and the skin spot evaluation program stored in the memory device 25. Further, the CPU 26 actualizes the skin spot evaluation process of the embodiment by controlling each of the hardware components to perform processes such as inputting and outputting data and controlling the entirety of the processes of the computer. Here, the various data or the like that are necessary when executing the program may be obtained from the auxiliary storage 24 and the executed result or the like may be stored therein.

The network connection device 27 obtains the skin spot evaluation program from another apparatus or the like that is connected to a communication network or the like typically the Internet, LAN (Local Area Network) or the like by connecting to the communication network or the like. Further, it is possible for the network connection device 27 to provide the executed result obtained by executing the program or the skin spot evaluation program itself of the embodiment to another apparatus or the like.

According to the hardware structure as described above, it is possible to perform the skin spot evaluation process of the embodiment. Further, the skin spot evaluation process of the embodiment can be easily actualized by a general purpose PC or the like by installing the skin spot evaluation program.

(Skin Spot Evaluation Process)

Figure 3:
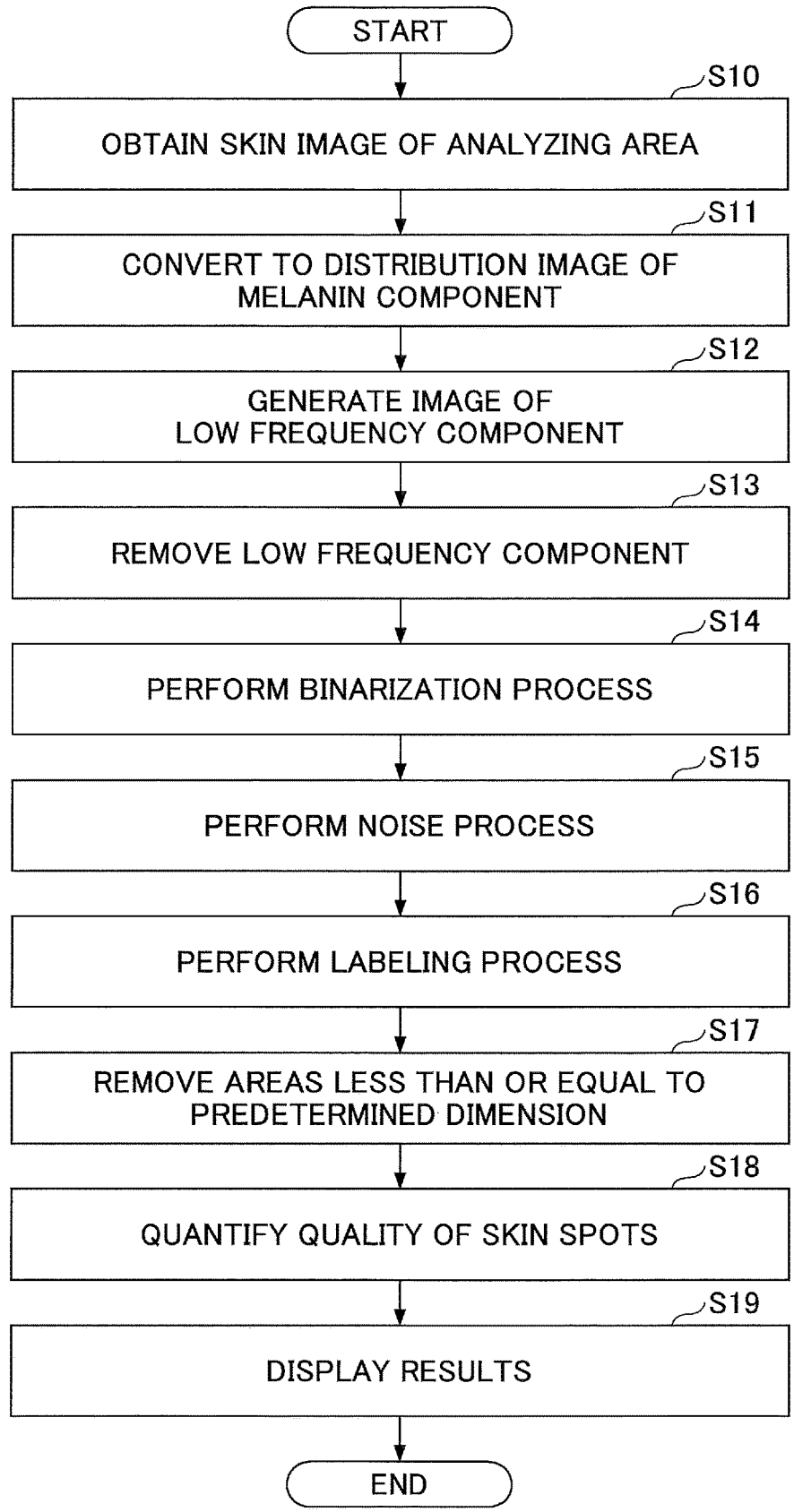
FIG. 3 is a flowchart illustrating an example of the skin spot evaluation process.

FIG. 3 is a flowchart illustrating an example of a skin spot evaluation process. As illustrated in FIG. 3, the skin spot evaluation apparatus 10, by the image obtaining unit 14, obtains a skin image of an analyzing area, a cheek area (an area of 500×500 pixels), for example, specified from a face image of a subject (S10).

Next, the skin spot evaluation apparatus 10, by the image processing unit 15, calculates a melanin component of the analyzing area specified in the process of S10, and converts to an image that indicates the calculated density of the melanin component and its distribution (a distribution image of the melanin component) (S11).

Next, the skin spot evaluation apparatus 10, by the image processing unit 15, generates an image of a low frequency component using a bandpass filter (Gaussian function or the like, for example), for example (S12), and subtracts it from the distribution image of the melanin component obtained in the process of S11 to remove the low frequency component (S13).

Next, the skin spot evaluation apparatus 10, by the image processing unit 15, performs a binarization process based on the melanin component (S14). By the process of S14, it is possible to differentiate high melanin portions and normal portions in the analyzing area.

Next, the skin spot evaluation apparatus 10, by the image processing unit 15, removes noise from the image (noise process) using a median filter on the distribution image of the melanin component, on which the binarization process is already performed (S15). Next, the skin spot evaluation apparatus 10, by the labeling processing unit 16, performs a labeling process by which an area where pixels with high melanin values continuously exist is labeled as a single pigmentation area (skin spot) (S16).

Next, the skin spot evaluation apparatus 10, by the labeling processing unit 16, removes areas whose dimension is less than or equal to predetermined dimension from the labeled pigmentation areas (S17). With this, small extracted areas such as pores wrongly extracted can be removed, for example.

Next, the skin spot evaluation apparatus 10, by the skin spot evaluation unit 17, quantifies a quality of the skin spots obtained by the processes until S17 by analyzing the number of the skin spots, a size of each of the skin spots, density of each of the skin spots or the like in the analyzing area, and using at least one of the analyzed number of the skin spots, the dimensions of the skin spots and the densities of the skin spots (S18). Next, the skin spot evaluation apparatus 10, by the image generation unit 18, generates a screen in which the result obtained in the process of S18 is displayed, displays it on the screen (S19), and finishes the process.

It is possible to appropriately evaluate a quality of the skin spots of the analyzing area by the above described skin spot evaluation process.

(Steps to Perform Binarization Process)

Figure 4A:
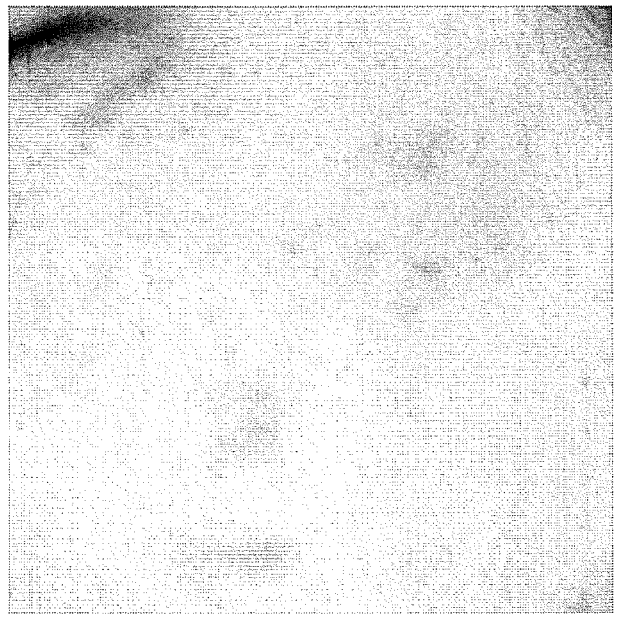
FIG. 4A is a view for describing steps to perform a binarization process on an analyzing area.
Figure 4B:
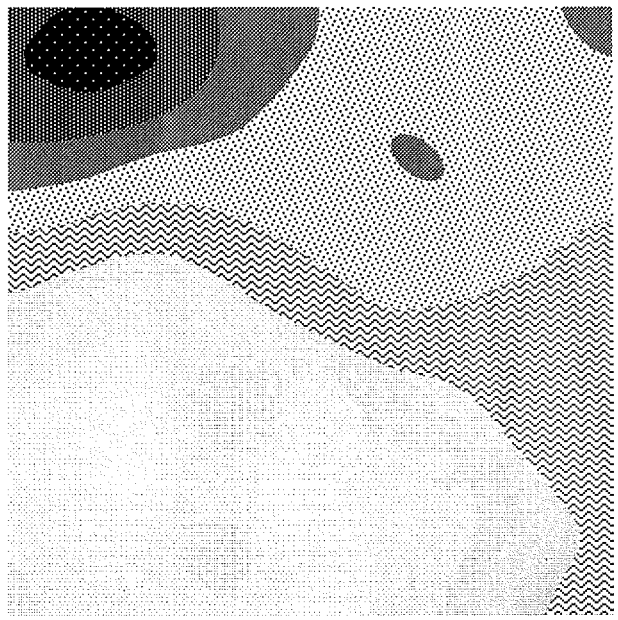
FIG. 4B is a view for describing steps to perform a binarization process on an analyzing area.
Figure 4C:
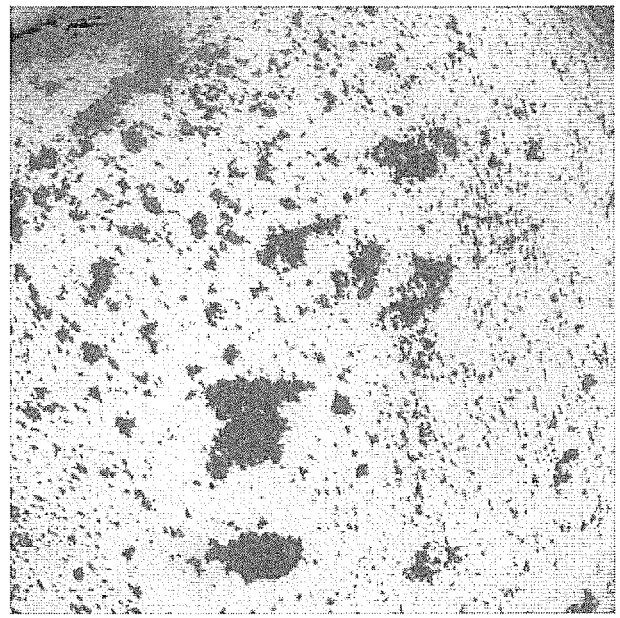
FIG. 4C is a view for describing steps to perform a binarization process on an analyzing area.

FIG. 4A to FIG. 4C are views for describing steps to perform a binarization process on the analyzing area. FIG. 4A illustrates an example of an analyzing area set in a skin image of a subject. FIG. 4B illustrates an example in which a process by a bandpass filter is performed on a distribution image of the melanin component calculated from the image illustrated in FIG. 4A. FIG. 4C illustrates an example of an image obtained by subtracting the image illustrated in FIG. 4B from the distribution image of the melanin component calculated from the image illustrated in FIG. 4A, and performing a binarization process.

Specifically describing, in an example of FIG. 4A, a cheek area (area of 500×500 pixels, for example) of a skin image of a subject is set as an analyzing area. For an example of FIG. 4A, an analyzing area is specified by placing a rectangular area composed of 500×500 pixels, for example, on the skin image of the subject such that a tail of the left eye of the subject matches a left upper corner of the rectangular, and a left wing of the nose of the subject matches a left lower corner of the rectangular. The image processing unit 15 calculates the melanin component from the analyzing area of the skin image illustrated in FIG. 4A, and converts it to an image (distribution image of the melanin component) that indicates the density of the melanin component and its distribution.

FIG. 4B is a view illustrating an example of an image of a low frequency component (bandwidth whose half width is greater than or equal to about 40.0 mm, for example) generated by performing a process by a bandpass filter on the distribution image of the melanin component calculated from the image of the analyzing area illustrated in FIG. 4A. It is possible to remove affection of shadow due to a shape of a face of the subject by subtracting the image of FIG. 4B from the distribution image of the melanin component calculated from FIG. 4A, for example FIG. 4C illustrates an example of an image obtained by performing a binarization process based on the melanin component on the analyzing area, for which the image illustrated in FIG. 4B is subtracted from the distribution image of the melanin component calculated from FIG. 4A. With this, as illustrated in FIG. 4C, it is possible to differentiate high melanin portions and normal portions in the analyzing area.

(Steps to Extract Skin Spots)

Figure 5A:
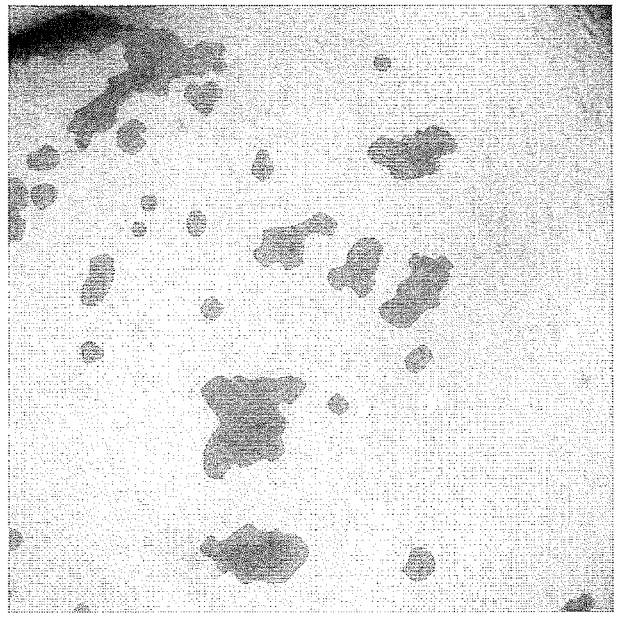
FIG. 5A is a view for describing steps to extract a skin spot.
Figure 5B:
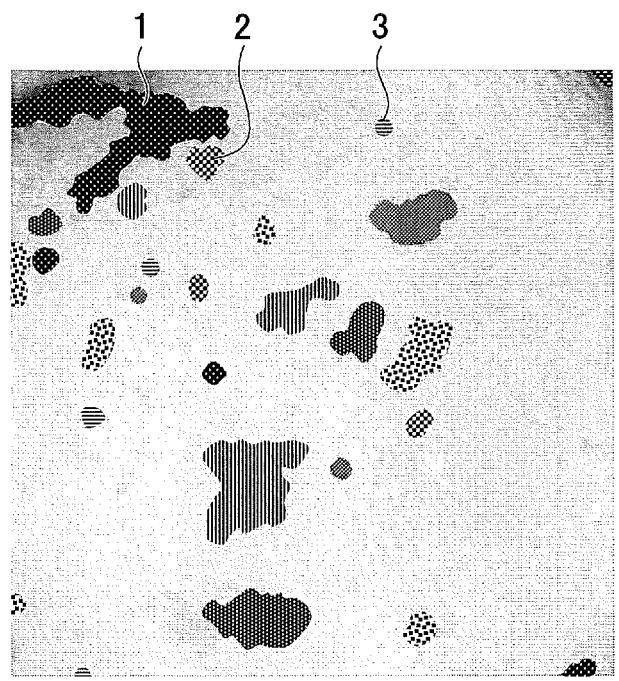
FIG. 5B is a view for describing steps to extract a skin spot.
Figure 5C:
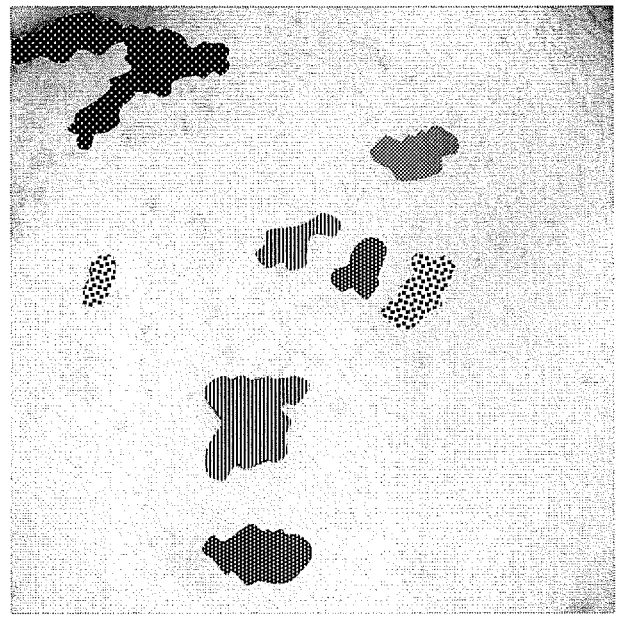
FIG. 5C is a view for describing steps to extract a skin spot.

FIG. 5A to FIG. 5C are views for describing steps to extract skin spots. FIG. 5A illustrates an example of the analyzing area on which a median filter process, as an example of a filter process, is performed, and FIG. 5B illustrates an example of the analyzing area on which the labeling process is performed. FIG. 5C illustrates an example of the analyzing area in which small areas (pores, for example) among the labeled areas are removed.

FIG. 5A illustrates an example of an image on which a median filter process using a filter of 5×5 pixels is performed on the analyzing area, on which the binarization process illustrated in FIG. 4C is already performed, for example. In the analyzing area illustrated in FIG. 5A, compared with the analyzing area illustrated in FIG. 4C, noise of the image is removed.

FIG. 5B illustrates an example of an image on which the labeling process, by which an area where pixels with high melanin values continuously exist is labeled as a single pigmentation area (skin spot), is performed on the analyzing area on which the median filter process illustrated in FIG. 5A is already performed. In an example of FIG. 5B, areas indicated by numbers "1", "2" and "3" are labeled.

FIG. 5C illustrates an example of an image from which areas less than or equal to predetermined dimension (less than or equal to 1.0 mm² or the like, for example) are removed from the analyzing area on which the labeling process illustrated in FIG. 5B is already performed. With this, as illustrated in FIG. 5C, small pigmentation areas such as pores, for example, are removed.

(Example of Labeled Skin Spots)

Figure 6A:
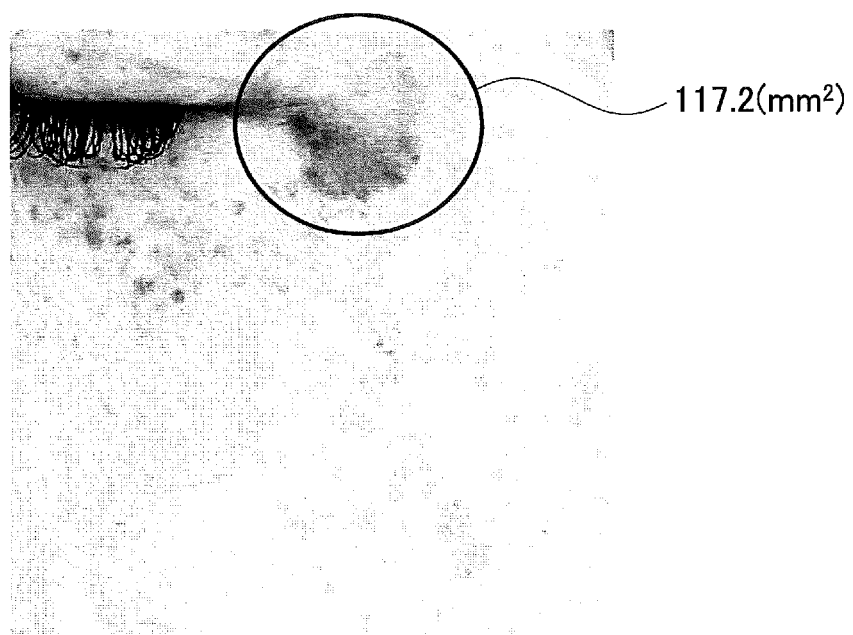
FIG. 6A is a view for describing dimension of an extracted skin spot.
Figure 6B:
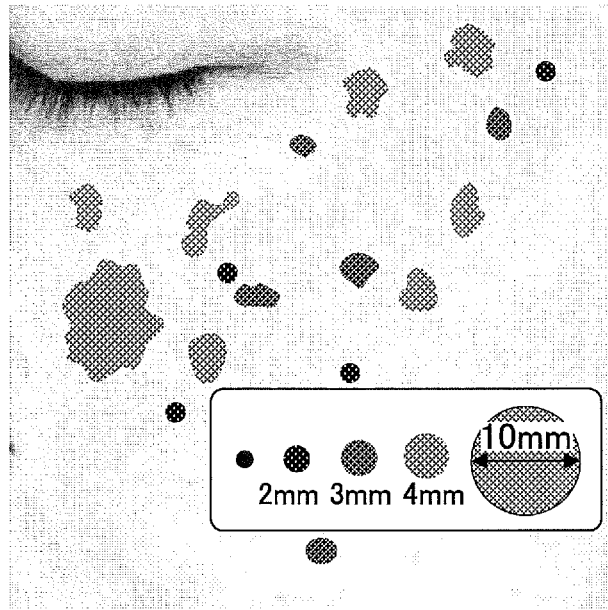
FIG. 6B is a view for describing dimension of an extracted skin spot.
Figure 6C:
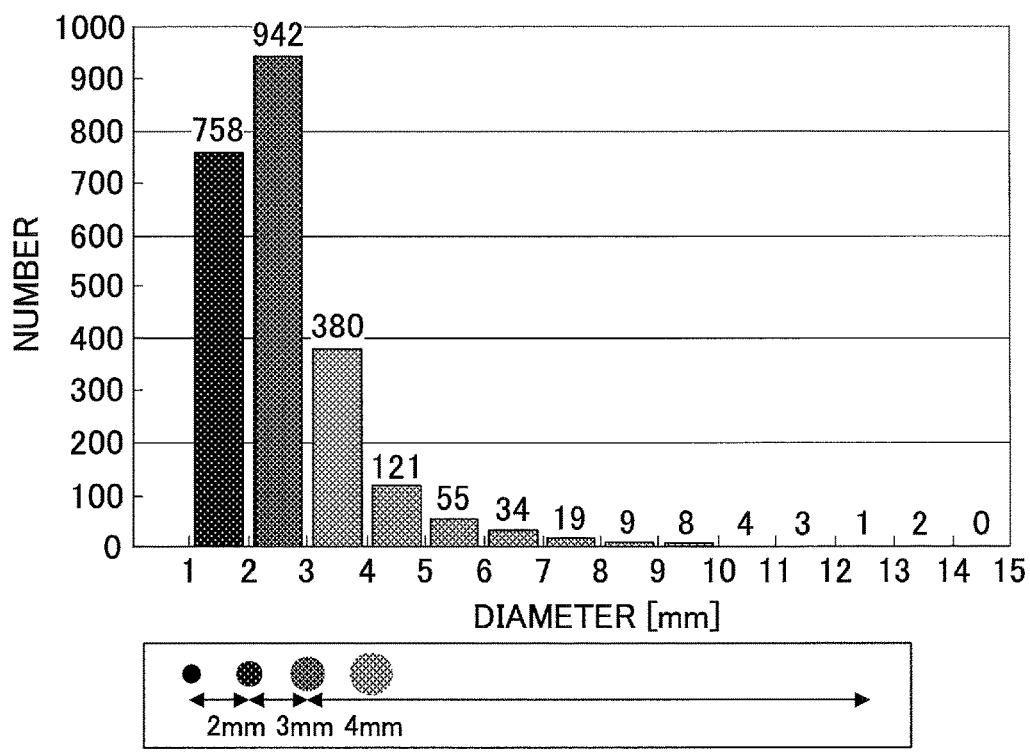
FIG. 6C is a view for describing dimension of an extracted skin spot.

Next, the skin spots labeled as described above are described. FIG. 6A to FIG. 6C are views for describing dimensions of the extracted skin spots. FIG. 6A is an example of a skin image in which a large skin spot is included, and dimension of the skin spot analyzed by the skin spot evaluation unit 17 is displayed. FIG. 6B is an example of a skin image of a cheek area, and the labeled skin spots are displayed for each dimension. FIG. 6C is an example of a distribution graph of the labeled skin spots for each dimension.

In the skin image illustrated in FIG. 6A, a circle that specifies a targeting skin spot and the dimension (117.2 mm²) of the skin spot are shown.

In the skin image illustrated in FIG. 6B, the labeled skin spots are shown by different colors based on the sizes of predetermined dimensions (diameter 2 mm, 3 mm, 4 mm and 10 mm, for example). Here, ranges of the dimensions (diameters) shown by different colors in the embodiment are not limited so. As described above, by labeling the skin spots, it is possible to obtain the dimension of each of the labeled skin spots based on an area (pixels) of the respective skin spot and the resolution of the image or the like. Further, it is possible to easily grasp the dimension of each of the skin spots, the total dimension of the skin spots at the cheek area or the like other than the targeting skin spot as well.

In the graph illustrated in FIG. 6C, distribution of skin spots for each dimension (diameter 2 mm to 15 mm) obtained from skin images of Japanese female of thirties to fifties is shown. In FIG. 6C, it is shown that, for Japanese female of thirties to fifties, skin spots with a diameter of 3 mm are included most as the dimensions of the skin spots. For example, by checking distribution of skin spots for each dimension of a skin image of a subject and displaying similarly as the graph of FIG. 6C, it is possible to grasp the quality of the skin spots of the subject.

In this embodiment, the image generation unit 18 generates an image as illustrated in FIG. 6A or FIG. 6B, and displays the generated image on a screen. Here, the image generation unit may display an aggregation result by a histogram or the like, similarly as FIG. 6C, for example, by aggregating the number of skin spots for each size (the dimension, the diameter or the like, for example) of the skin spot, or by aggregating the number of skin spots for each density (melanin amount) of the skin spot, for example.

As such, according to the embodiment, the skin spots can be appropriately evaluated by generating data obtained by quantifying characteristics of the skin spots such as the number of skin spots, dimension of each of the skin spots, or density of each of the skin spots in the skin image. Furthermore, for example, the skin spots can be appropriately evaluated by generating data obtained by quantifying characteristics of the skin spots such as the number of the skin spots whose dimensions are greater than or equal to predetermined dimension, the number of the skin spots whose density (melanin amount) is greater than or equal to predetermined density or the like.

(Analysis of the Number of Skin Spots and Dimensions of Skin Spots for Each Generation)

Figure 7A:
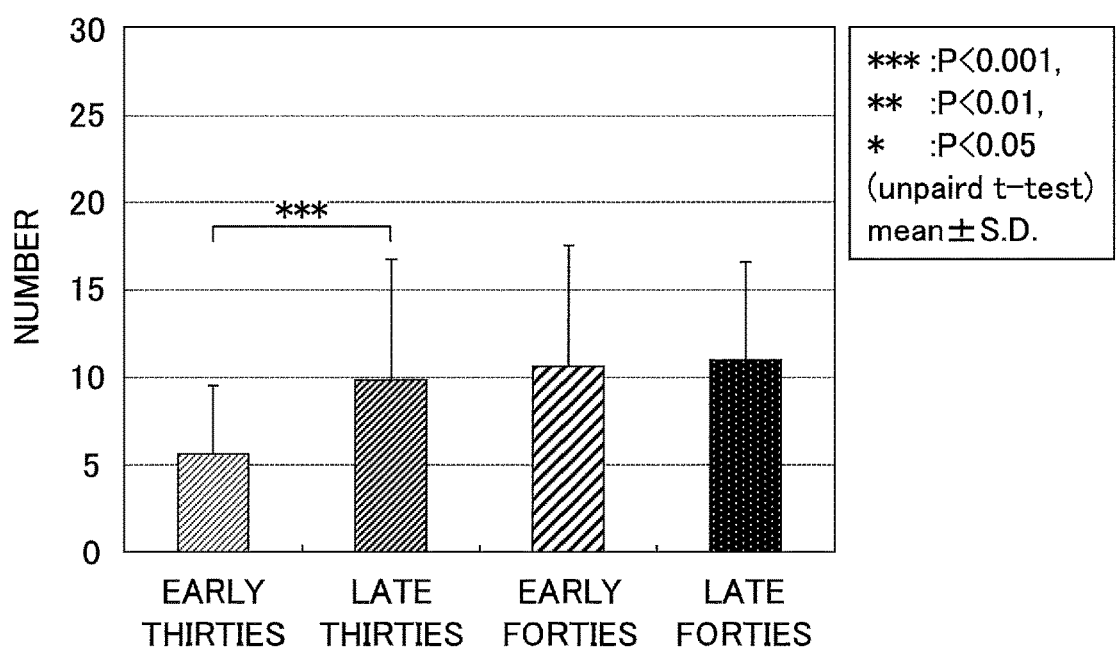
FIG. 7A is a view illustrating results obtained by analyzing the number of skin spots and dimension of each of the skin spots for each generation.
Figure 7B:
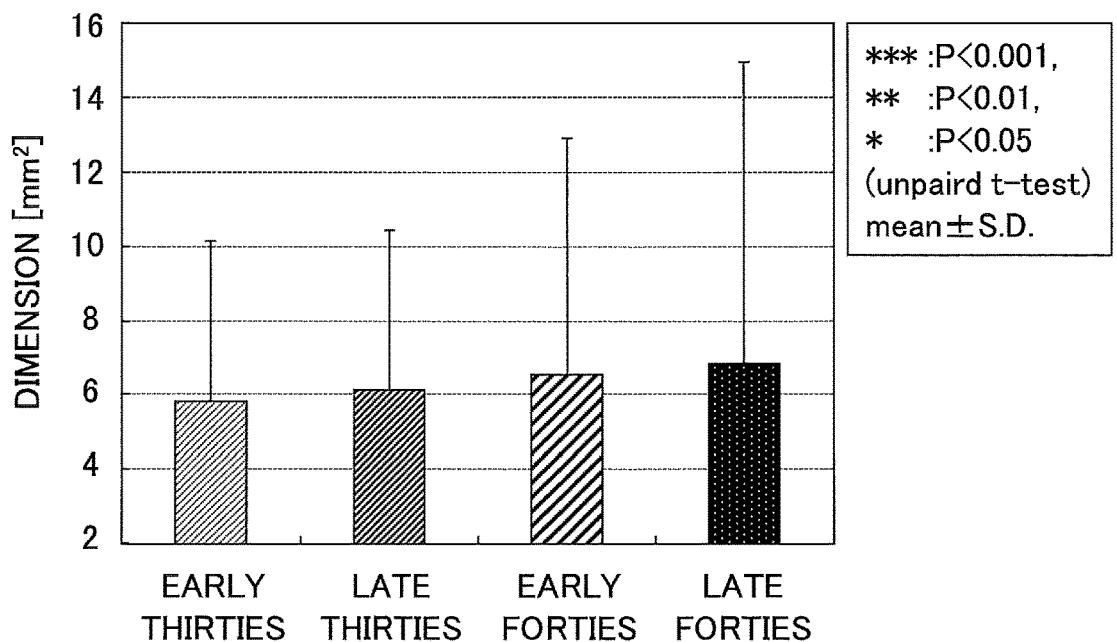
FIG. 7B is a view illustrating results obtained by analyzing the number of skin spots and dimension of each of the skin spots for each generation.
Figure 7C:
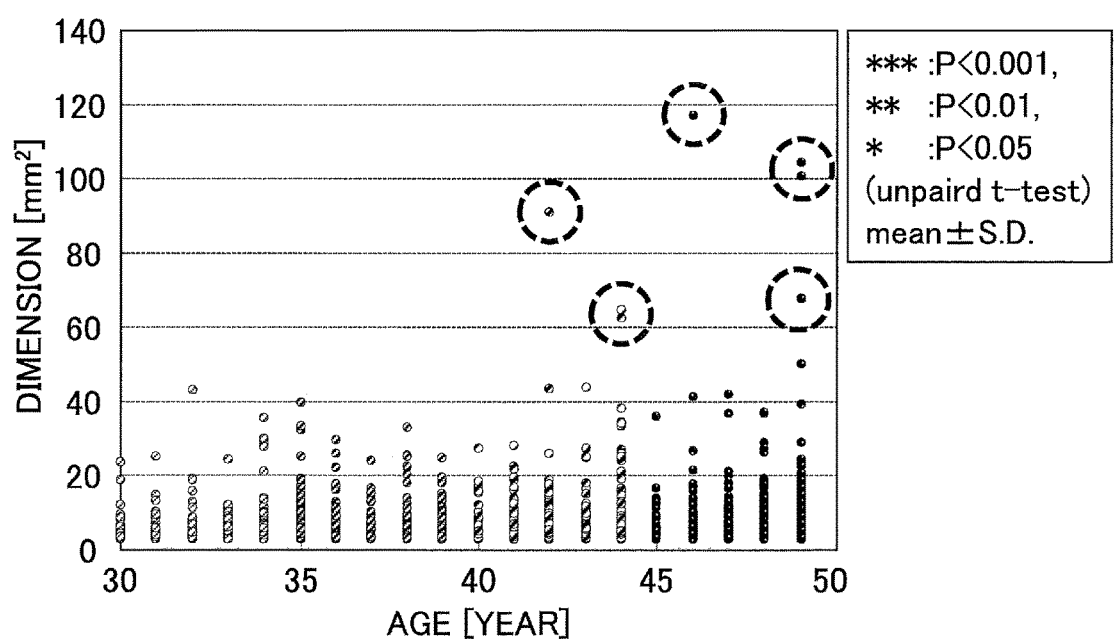
FIG. 7C is a view illustrating results obtained by analyzing the number of skin spots and dimension of each of the skin spots for each generation.
Figure 8A:
FIG. 8A is a view illustrating a skin image in which labeled skin spots are shown for each generation.
Figure 8A:
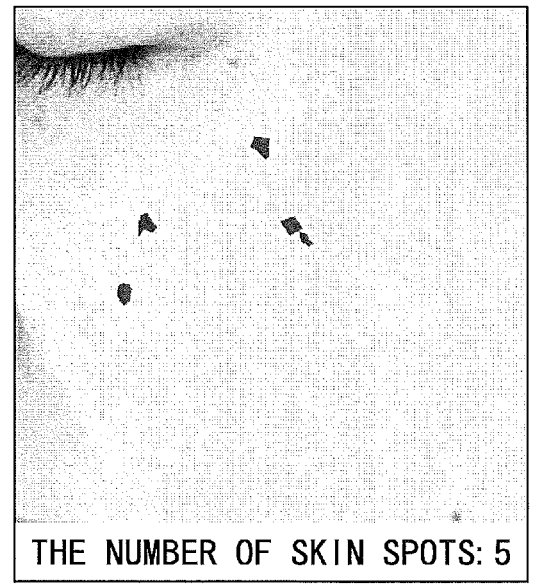

Next, an example of analysis or evaluation of skin spots by obtaining the number of the skin spots labeled as described above and the dimension of each of the skin spots for each generation of subjects. FIG. 7A to FIG. 7C are views illustrating results obtained by analyzing the number of skin spots and dimension of each of the skin spots for each generation. FIG. 8A to FIG. 8O are views illustrating skin images of each generation, and are views illustrating skin images in which labeled skin spots are shown.

FIG. 7A is a graph illustrating the number of skin spots per person for each generation. FIG. 7B is a graph illustrating average dimension of the skin spots for each generation. FIG. 7C is a graph illustrating distribution of dimensions of the skin spots for each generation.

In an example of FIG. 7A, the number of skin spots of skin images of subjects of early thirties, late thirties, early forties and late forties are illustrated. According to an evaluation result of the skin spots of the embodiment, as illustrated in FIG. 7A, the number of the skin spots gradually increases from early thirties, and for late forties, compared with early thirties, the number of the skin spots is increased about twice. Further, in particular, the number of the skin spots is jumped from early thirties to late thirties.

In an example of FIG. 7B, similar to FIG. 7A, average of dimension of the skin spots in the skin images of subjects of each of early thirties, late thirties, early forties and late forties. Further, in an example of FIG. 7C, dimension of each of the skin spots is plotted by subdividing ages of the subjects into each age.

As illustrated in FIG. 7B, for the early thirties to the late forties, average dimension of the skin spots is slightly increased (no significance). On the other hand, in FIG. 7C, it can be understood that skin spots of large dimension, which are not included in the skin images of the subjects of thirties, are included in the skin images of the subjects of the late forties (dotted portions in FIG. 7C).

Figure 8B:
FIG. 8B is a view illustrating a skin image in which labeled skin spots are shown for each generation.
Figure 8B:
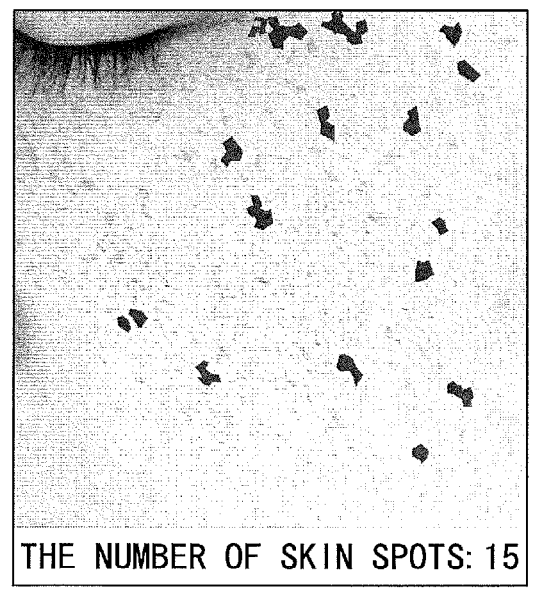
Figure 8C:
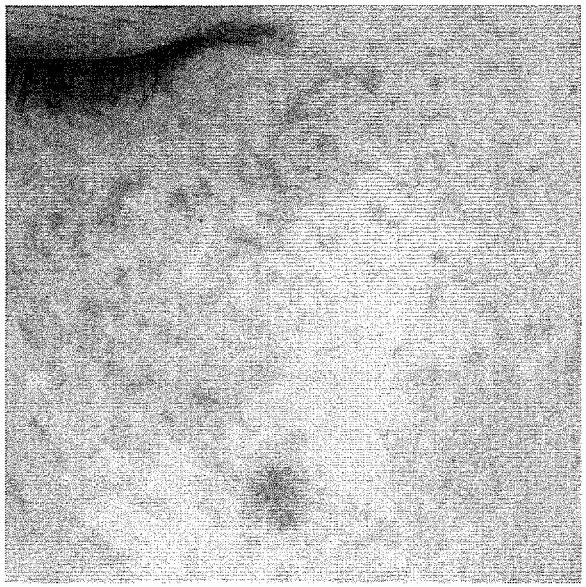
FIG. 8C is a view illustrating a skin image in which labeled skin spots are shown for each generation.
Figure 8C:
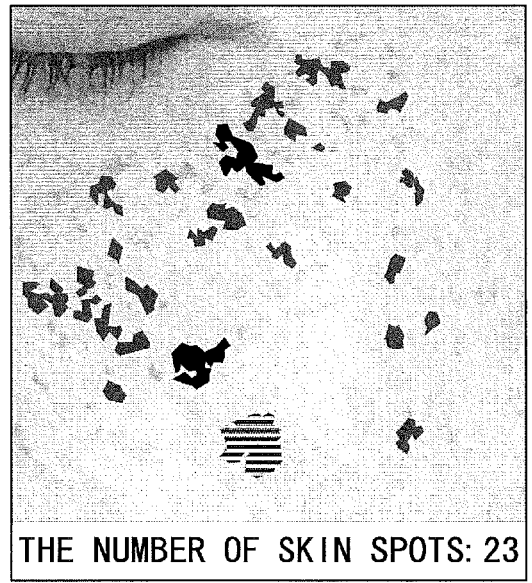

FIG. 8A illustrates an example of a skin image of a subject of 30 years old. FIG. 8B illustrates an example of a skin image of a subject of 35 years old. FIG. 8C illustrates an example of a skin image of a subject of 48 years old. Here, in FIG. 8A to FIG. 8C, an example in which the areas in the skin image extracted by the image generation unit 18 as the skin spots are displayed by different colors in accordance with the size (dimension, diameter or the like, for example) of each of the skin spots to be overlapped on the skin image.

When comparing the skin image of the subject of 30 years old illustrated in FIG. 8A and the skin image of the subject of the subject of 35 years old illustrated in FIG. 8B, the number of skin spots is increased by three times. Further, the skin image of the subject of 48 years old illustrated in FIG. 8C includes larger skin spots compared with skin spots of the skin image of the subject of 30 years old illustrated in FIG. 8A or the skin image of the subject of 35 years old illustrated in FIG. 8B.

As described above, by analyzing the number of skin spots or its dimension for each generation of the subjects, it is possible to grasp at which timing and how the quality of the skin spots changes such as the number of skin spots is largely increased from the early thirties to the late thirties, or the large skin spots are generated for the early forties or the late forties.

(Analysis of Densities of Skin Spots for Each Generation)

Next, an example is described in which the density of each of the labeled skin spots as described above is obtained for each generation of the subjects, and the analysis and the evaluation of the skin spots are performed. FIG. 9 is a view illustrating a result obtained by analyzing the densities of the skin spots based on the melanin amount.

In an example of FIG. 9, melanin amounts of skin spots (pigmentation areas) in skin images of the early thirties, the late thirties, the early forties and the late forties are illustrated. According to the analyzed result of the embodiment, it can be understood that the melanin amount is increased as the age of the subject increases. Further, it can be understood that the melanin amount of areas that are determined to be the above described normal portions (normal skin color) is also increased as the age of the subject increases.

As described above, by analyzing the density of the skin spots for each generation of the subjects, it is possible to grasp how the characteristic of the skin spots changes in accordance with age. For example, it can be understood that as the density of the skin spots becomes high as the age increases, and the color of the skin color areas, other than the areas extracted as the skin spots, is also becomes high (dark), distinguishability (difference) of the skin spots is not changed, or the like.

As such, as it is possible to grasp the change of the characteristic of the skin spots based on the number of skin spots, the size of the skin spots, the density of the skin spots or the like for each generation of the subjects, it is possible to use data regarding the skin spots extracted from the skin image of each of the subjects can be used as basic data for countermeasures for skin spots for each generation, for example.

Further, it is possible to grasp change of the characteristic of the skin spots for each season by continuously analyzing the characteristic of the skin spots of the skin of the subject, for example. Further, other than each generation, each season or the like, it is possible to grasp change of the characteristic of the skin spots for each occupation, for example.

Here, each of the above described images of FIG. 5A to FIG. 9 may be generated by the image generation unit 18, and it is possible to appropriately grasp the characteristic of the skin spots by displaying the generated image on a screen of the output unit 12 or the like.

As described above, according to the embodiment, it is possible to grasp the quality (characteristic) of the skin spots, and appropriately evaluate the skin spots.

Here, although it is described that the skin image (cheek area, for example) is obtained from the face image of the subject in the above described embodiment, this is not limited so. For example, the skin image may be obtained from an image obtained by photographing the neck, the arm or the like of the subject.

The present invention is not limited to the specifically disclosed embodiments, and numerous variations and modifications may be made without departing from the spirit and scope of the present invention.

The present application is based on and claims the benefit of priority of Japanese Priority Application No. 2014-234938 filed on Nov. 19, 2014, the entire contents of which are hereby incorporated by reference.

NUMERALS

10 skin spot evaluation apparatus
11 input unit
12 output unit
13 storing unit
14 image obtaining unit
15 image processing unit
16 labeling processing unit
17 skin spot evaluation unit
18 image generation unit
19 control unit
21 input device
22 output device
23 drive device
24 auxiliary storage
25 memory device
26 CPU
27 network connection device
28 recording medium

What is claimed is:

1. A skin spot evaluation apparatus comprising:
a memory; and
a processor coupled to the memory, wherein
the processor is configured
to generate pigment images indicative of distribution of a pigment component from skin images obtained by photographing skins of a plurality of subjects,
to apply bandpass filtering to the pigment images to remove low-frequency components therefrom to produce filtered pigment images,
to binarize the filtered pigment images based on concentration of the pigment component to produce binarized pigment images,
to apply a median filter to the binarized pigment images to remove noise therefrom to produce noise-removed binary pigment images that includes pixels having a low pigment value and pixels having a high pigment value,
to extract groups of combined pixels from the noise-removed binary pigment images by connecting together only contiguous pixels among the pixels having the high pigment value in the noise-removed binary pigment images that includes the pixels having the low pigment value and the pixels having the high pigment value,
to label the groups of combined pixels as skin spot areas, and remove areas whose dimension is less than or equal to a predetermined dimension from the skin spot areas to retain, as labeled skin spot areas, all areas whose dimension is greater than the predetermined dimension among the skin spot areas,
to generate a screen in which the skin spot areas labeled by the processor are displayed,
to obtain and analyze a number of the skin spots in the labeled skin spot areas, dimension of each of the skin spots and density of each of the skin spots based on melanin amounts for each generation of the plurality of subjects, and
to generate data obtained by quantifying a change over time of a characteristic of the skin spots of the plurality of skin images using an analyzed result,
wherein the processor is configured
to display the labeled skin spots by different colors based on predetermined dimension or diameter of each of the skin spot areas, the colors overlapping the skin spots on a skin image of a subject of the plurality of subjects, and
to display a first graph indicating the change over time of the characteristic of the skin spots in accordance with ages of the plurality of subjects, using the number of skin spots in the labeled skin spot areas, dimension of each of the skin spots and density of each of the skin spots, and wherein a second graph is generated by plotting dimension of each of the skin spots and breaking down each generation age group on a per subject age basis.

2. The skin spot evaluation apparatus according to claim 1, wherein the processor is configured to extract the skin spot areas based on values of a melanin component obtained by analyzing the skin image.

3. The skin spot evaluation apparatus according to claim 1, wherein the processor is configured to display a distribution graph of the skin spot areas labeled by the processor for each dimension or each diameter.

4. A non-transitory computer readable medium storing a program for causing a computer to function as a skin spot evaluation apparatus comprising:

a memory; and a processor coupled to the memory, wherein the processor is configured to generate pigment images indicative of distribution of a pigment component from skin images obtained by photographing skins of a plurality of subjects, to apply bandpass filtering to the pigment images to remove low-frequency components therefrom to produce filtered pigment images, to binarize the filtered pigment images based on concentration of the pigment component to produce binarized pigment images, to apply a median filter to the binarized pigment images to remove noise therefrom to produce noise-removed binary pigment images that includes pixels having a low pigment value and pixels having a high pigment value, to extract groups of combined pixels from the noise-removed binary pigment images by connecting together only contiguous pixels among the pixels having the high pigment value in the noise-removed binary pigment images that includes the pixels having the low pigment value and the pixels having the high pigment value, to label the groups of combined pixels as skin spot areas, and remove areas whose dimension is less than or equal to a predetermined dimension from the skin spot areas to retain, as labeled skin spot areas, all areas whose dimension is greater than the predetermined dimension among the skin spot areas, to generate a screen in which the skin spot areas labeled by the processor are displayed, to obtain and analyze a number of the skin spots in the labeled skin spot areas, dimension of each of the skin spots and density of each of the skin spots based on melanin amounts for each generation of the plurality of subjects, and to generate data obtained by quantifying a change over time of a characteristic of the skin spots of the plurality of skin images using an analyzed result, wherein the processor is configured to display the labeled skin spots by different colors based on predetermined dimension or diameter of each of the skin spot areas, the colors overlapping the skin spots on a skin image of a subject of the plurality of subjects, and to display a first graph indicating the change over time of the characteristic of the skin spots in accordance with ages of the plurality of subjects, using the number of skin spots in the labeled skin spot areas, dimension of each of the skin spots and density of each of the skin spots, and wherein a second graph is generated by plotting dimension of each of the skin spots and breaking down each generation age group on a per subject age basis.

5. The program according to claim 4, wherein the processor is configured to extract the skin spot areas based on values of a melanin component obtained by analyzing the skin image.

6. The program according to claim 4, wherein the processor is configured to display a distribution graph of the skin spot areas labeled by the processor for each dimension or each diameter.

* * * * *